US010022190B2

(12) United States Patent
Valsamis et al.

(10) Patent No.: US 10,022,190 B2
(45) Date of Patent: Jul. 17, 2018

(54) OPTICAL FORCE TRANSDUCER

(71) Applicants: UNIVERSITE LIBRE DE BRUXELLES, Brussels (BE); UNIVERSITE DE MONS, Mons (BE)

(72) Inventors: Jean-Baptiste Valsamis, Brussels (BE); Nicolas Cauche, Brussels (BE); Jacques Deviere, Braine le Comte (BE); Christophe Caucheteur, Mons (BE); Valérie Voisin, Mons (BE)

(73) Assignees: UNIVERSITE LIBRE DE BRUXELLES, Brussels (BE); UNIVERSITE DE MONS, Mons (BE)

( * ) Notice: Subject to any disclaimer, the term of this patent is extended or adjusted under 35 U.S.C. 154(b) by 542 days.

(21) Appl. No.: 14/377,443

(22) PCT Filed: Apr. 2, 2013

(86) PCT No.: PCT/EP2013/056919
§ 371 (c)(1),
(2) Date: Aug. 7, 2014

(87) PCT Pub. No.: WO2013/150019
PCT Pub. Date: Oct. 10, 2013

(65) Prior Publication Data
US 2016/0022373 A1    Jan. 28, 2016

(30) Foreign Application Priority Data
Apr. 4, 2012  (EP) .................................. 12163165

(51) Int. Cl.
*A61B 19/00*    (2006.01)
*A61B 5/22*    (2006.01)
(Continued)

(52) U.S. Cl.
CPC ............ *A61B 19/5244* (2013.01); *A61B 5/22* (2013.01); *A61B 5/6852* (2013.01);
(Continued)

(58) Field of Classification Search
CPC .... A61B 2034/2061; A61B 2562/0266; G01L 1/246; G01B 11/18; G01D 5/35312; G01D 5/35316; G01D 5/35319
See application file for complete search history.

(56) References Cited

U.S. PATENT DOCUMENTS 8,622,935 B1 * 1/2014 Leo .................... A61B 5/6843
600/585
2007/0156019 A1    7/2007 Larkin et al.
(Continued)

FOREIGN PATENT DOCUMENTS

| JP | 2003-177011 | 6/2003 |
|---|---|---|
| WO | WO 2009/007857 | 1/2009 |
| WO | WO 2010/079418 | 7/2010 |

OTHER PUBLICATIONS

International Search Report from International Application No. PCT/EP2013/056919 dated Jul. 22, 2013.

*Primary Examiner* — Blake A Tankersley
*Assistant Examiner* — Ruben Parco, Jr.
(74) *Attorney, Agent, or Firm* — Merchant & Gould P.C.

(57) ABSTRACT

Force transducer (10) include two structural members (11, 12) spaced apart to define a gap (101) and being linked to each other. Optical fibers (13) are to the members and are freely suspended in the gap. The optical fibers are configured to provide a change in a detectable optical property responsive to a change in relative position between the two members in one or more predetermined degrees of freedom. Each of the optical fibers (13) is fixed to both structural members and continuous between the members to link the two structural members to each other. The optical fibers are
(Continued)

substantially the only structure forming a link between the two structural members (11, 12), such that the arrangement of the optical fibers defines substantially the stiffness of the link between the two structural members in the one or more predetermined degrees of freedom, which stiffness is mainly, such as for at least 95%, determined by the optical fibers.

17 Claims, 9 Drawing Sheets

(51) Int. Cl.
    *G01L 5/16*     (2006.01)
    *G01L 1/24*     (2006.01)
    *A61B 5/00*     (2006.01)
    *G01B 11/16*    (2006.01)
    *A61B 34/20*    (2016.01)
    *G01D 5/353*    (2006.01)
    *A61B 90/00*    (2016.01)

(52) U.S. Cl.
    CPC ............ *A61B 5/6885* (2013.01); *A61B 34/20* (2016.02); *A61B 90/06* (2016.02); *G01B 11/18* (2013.01); *G01D 5/35377* (2013.01); *G01L 1/246* (2013.01); *G01L 5/166* (2013.01); *A61B 2034/2061* (2016.02); *A61B 2090/064* (2016.02); *A61B 2562/0266* (2013.01); *G01D 5/353* (2013.01)

(56) References Cited

U.S. PATENT DOCUMENTS

| | | | |
|---|---|---|---|
| 2009/0123111 A1* | 5/2009 | Udd | A61B 5/06 385/13 |
| 2009/0177095 A1 | 7/2009 | Aeby et al. | |
| 2009/0287092 A1* | 11/2009 | Leo | A61B 5/00 600/474 |
| 2009/0324161 A1 | 12/2009 | Prisco | |
| 2010/0030063 A1 | 2/2010 | Lee et al. | |
| 2010/0296772 A1* | 11/2010 | Arkwright | A61B 5/037 385/13 |
| 2011/0090486 A1 | 4/2011 | Udd | |
| 2012/0011917 A1 | 1/2012 | Verbruggen | |

\* cited by examiner

OPTICAL FORCE TRANSDUCER

This application is a National Stage Application of PCT/EP2013/056919, filed 2 Apr. 2013, which claims benefit of Ser. No. 12/163,165.9, filed 4 Apr. 2012 in Europe and which applications are incorporated herein by reference. To the extent appropriate, a claim of priority is made to each of the above disclosed applications.

BACKGROUND OF THE INVENTION

The present invention is related to a force transducer capable of measuring a force and/or moment exerted upon it according to one or several directions. Use is made of optical fibres which are strained when a force is acting on the transducer and which are configured to provide a change in a detectable optical property responsive to the strain. In particular, the force transducer according to the invention is configured for use in minimally invasive surgery, such as for measuring forces acting at the distal end of a catheter.

Nowadays, the trend in surgery is to operate in a minimally invasive way inside the patient in order to reduce trauma and potential complications. In gastroenterology, the use of endoscope allows the surgeon to work with a set of medical tools (knives, needles, etc.) inside the digestive system.

When using an endoscope, the manipulation of the catheter driving any medical tool is subject to parasitic forces, such as the friction between the catheter and the endoscope, the elastic force due to the change of curvature of the catheter and the body of the medical tool. Consequently, the force felt by the surgeon through the catheter is not the force exerted by the tool on the patient body. There is therefore need of a force measurement system in order to feed back the force exerted by the medical tool on the patient body. This requires the force to be measured as distally as possible on the tool.

To this end, force transducers are known from WO 2009/007857, which comprise two base portions spaced apart by one or more standoff members and a trio of strain sensing elements. The strain sensing elements can include optical fibres potted in the base portions and defining interferometric gaps between a transmitting part of optical fibre and a receiving element, which may act as extrinsic Fabry-Perot interferometers (optical fibres are not stressed).

The standoff member can assume different forms and serves the purpose of (weak) link between the base portions, so that when a force is acting on one of the base portions, the interferometric gap is altered and a measurement can be performed. The standoff member has a coefficient of thermal expansion similar to that of the strain sensing elements to render the measurement insensitive to bulk temperature changes, and can be made of a same material. However, it may be difficult and/or expensive to provide a standoff member of same or similar material as the optical fibre and in a desired shape.

WO 2010/079418 describes, relating to FIGS. 17-21, another force transducer of the above type, which comprises a structural member defined by segments linked to one another by flexures defining a serial arrangement of gaps in the structural member. A plurality of optical fibres are attached to the segments and comprise Fabry-Perot or Bragg grating strain sensors to measure the change of distance between the segments. When the structural member is deformed by a force acting on it, the optical fibres are strained, which is sensed by the strain sensors shifting the wavelength of the reflected light.

Such force transducers have the advantage that they can be made very small, with representative dimensions in the order of magnitude of a few millimeters, so that they can be incorporated at the distal end of a catheter and be inserted without any problem through the lumen of an endoscope.

A disadvantage however, is that the optical fibres have different lever arms relative to the structural member for each optical fibre, which complicates force measurement. The transducer moreover has a limited size below which the structural member does not present an appropriate stiffness to measure usual force in minimally invasive surgery.

Another disadvantage of the above force transducers, is that, considering the small dimensions, they are relatively difficult to manufacture, and consequently, their manufacture is costly.

SUMMARY OF THE INVENTION

It is therefore an aim of the invention to provide a force transducer for use in minimally invasive surgery, which overcomes the drawbacks of prior art force transducers.

In particular, it is an aim of the invention to provide a force transducer of the above type, which is highly sensitive in a number of predetermined degrees of freedom.

It is an aim of the invention to provide a force transducer of the above type, which is of simple structure and easy to manufacture and therefore cost-effective.

It is an aim of the invention to provide a force transducer of the above type, of which the required stiffness of a structural member does not substantially impose a limitation on the overall size of the transducer.

Force transducers of the invention comprise two structural members and a plurality of optical fibres. The structural members are spaced apart, thus defining a gap between them, and are linked to each other. The plurality of optical fibres are fixed to the structural members and are freely suspended in the gap between the members. At least two of the optical fibres are configured to provide a change in a detectable optical property responsive to a change in relative position between the two members in one or more predetermined degrees of freedom.

According to an aspect of the invention, each of said plurality of optical fibres is fixed to both structural members and continuous between the members so as to link the two structural members to each other. There are advantageously at least three, advantageously at least four optical fibres fixed to both structural members and briding the gap between them. According to a further aspect of the invention, the plurality of optical fibres are substantially the only structure forming a link between the two structural members. This means that the assembly of the plurality of optical fibres, i.e. their number, disposition, sizes and lengths of free suspension define substantially the stiffness of the link between the two structural members in the one or more predetermined degrees of freedom, which stiffness is mainly, such as for at least 95%, determined by the plurality of optical fibres.

Hence, unlike the prior art, wherein structural members are attached to each other by other means, in addition to the optical fibres, in force transducers of the invention the optical fibres both determine the stiffness of the link between the members and are used for performing a measurement. As a result, the structural complexity of the force transducers, and hence cost, is reduced, whereas measurement accuracy can be improved.

BRIEF DESCRIPTION OF THE DRAWINGS

Aspects of the invention will now be described in more detail with reference to the appended drawings, wherein.

DETAILED DESCRIPTION OF THE PREFERRED EMBODIMENT(S)

Figure 1:
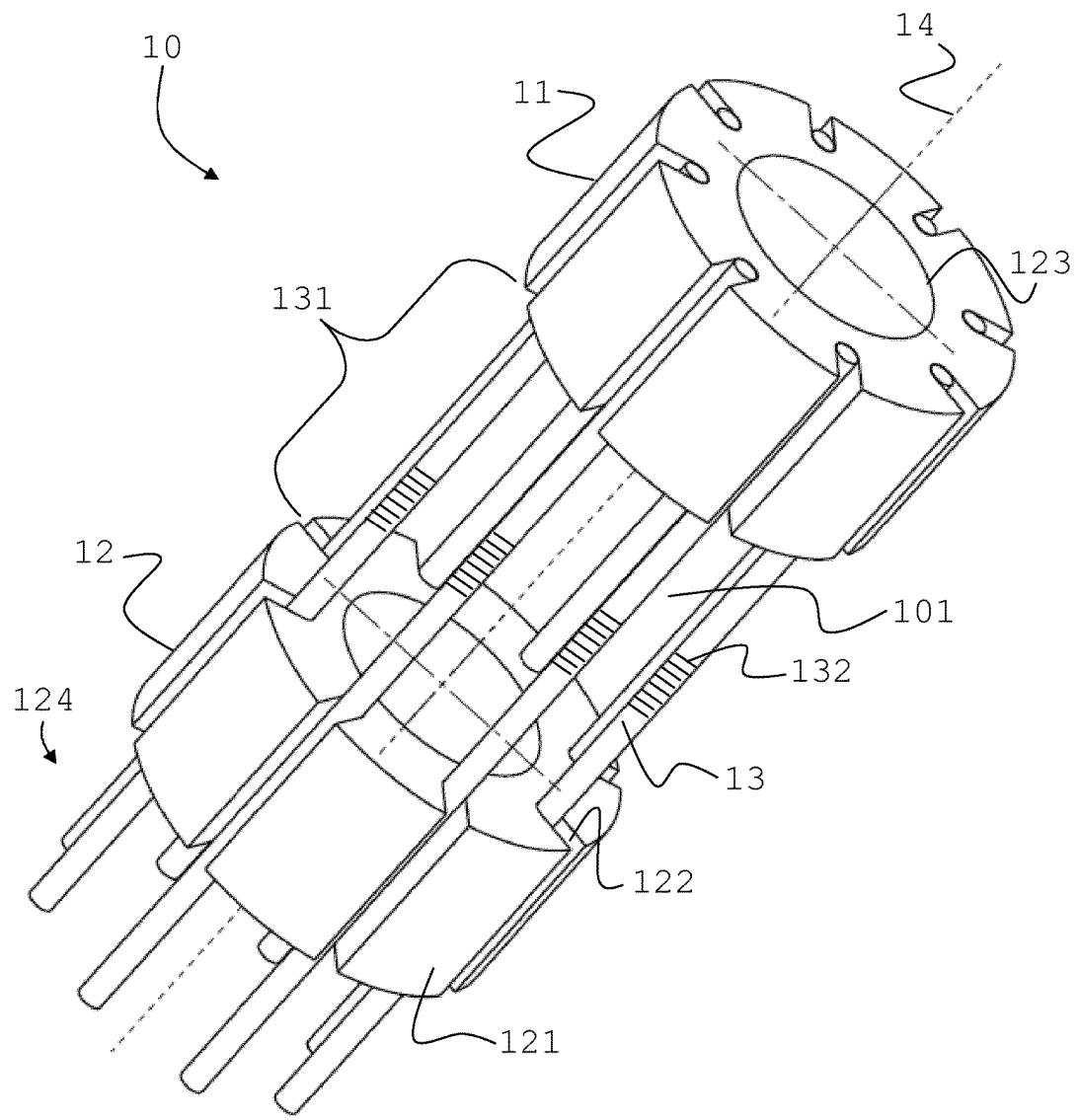
FIG. 1 represents a perspective view of a force transducer according to the invention.

FIG. 1 represents an assembled force transducer according to the invention. Force transducer 10 comprises (at least) two separate and spaced apart members 11 and 12. The spacing between members 11 and 12 defines a gap 101 between the two. Advantageously, the members 11 and 12 are kept at a distance solely by a multitude of optical fibres 13, which extend between the members 11 and 12 and hence bridge the gap 101. Each one optical fibre 13 is secured to both structural members 11 and 12, and is freely suspended between them.

Members 11 and 12 serve a structural purpose, since a force will act on either one of them. They are advantageously designed to be ideally rigid, such that they do not substantially deform under the range of forces which the transducer 10 is designed to measure. According to the invention, a force acting on one of the members 11, 12 will cause a relative displacement between the two structural members 11 and 12. Since the optical fibres are secured to both the members 11 and 12, the displacement will strain the optical fibres 13 between the points of attachment to the members 11 and 12. By providing strain detection means in or along the optical fibres 13 between those points of attachment, a strain measurement can be made, which can be correlated to the force.

Therefore, in order to provide a high accuracy in the force measurement, the members 11 and 12 are advantageously made as rigid as geometrical constraints permit.

According to the invention, no structure other than the optical fibres 13 provides a substantial link between the two members 11 and 12. Advantageously, the gap 101 between the structural members extends along the entire perimeter of the structural members 11 and 12, or, in other words, the members 11, 12 are spaced apart throughout their (overlapping) cross sectional areas. It is duly noted that this may apply only to those degrees of freedom along which the transducer is configured to perform a measurement. Force transducers according to the invention may be configured to measure forces along or about some but not all axes of movement. Furthermore, suitable mechanical constraints between the members 11 and 12 may be provided for preventing relative deformation between structure elements along or about those axes where the transducer is not configured for performing measurements. Hence, force transducers according to the invention may have less than six degrees of freedom and force measurement may not be configured for all degrees of freedom.

The overall rigidity of the transducer—in the directions of measurement—is mainly, and advantageously substantially entirely, due to the optical fibres 13. As a result, force transducers can be made which can be very sensitive and can provide very accurate measurements. Furthermore, no special weak or deformable structure is provided, such that transducers of the invention are of simple construction and therefore easy to manufacture.

Hence, according to the invention, the length 131 of the optical fibres 13 which is freely suspended between the members 11 and 12, together with the number, size and disposition of the optical fibres 13, will determine to a large extent the rigidity of the link between the two members 11 and 12 of the force transducer in those degrees of freedom according to which the force transducer is designed to measure forces. The rigidity of the link between members 11 and 12 along those degrees of freedom configured for force measurement is mainly, and advantageously for at least 95%, advantageously for at least 97.5%, advantageously for at least 99%, advantageously for at least 99.9%, determined by the disposition of the optical fibres 13. The above rigidity refers to the stiffness of the link between the two members 11 and 12.

The number of optical fibres 13 secured to both structural members 11, 12, and extending continuously between them is at least two, advantageously at least three, advantageously at least four.

In order to avoid that the link between the two members 11 and 12 would be too weak, the number, size and disposition of the optical fibres 13 should be chosen such that, within the operable range of forces of the transducer, the optical fibres do not substantially deflect and no buckling of the optical fibres occurs. It is possible to provide one or both members with a protective structure for the optical fibres preventing excessive deformation (bending, buckling) and even rupture in case of misuse or excessive force.

Figure 2:
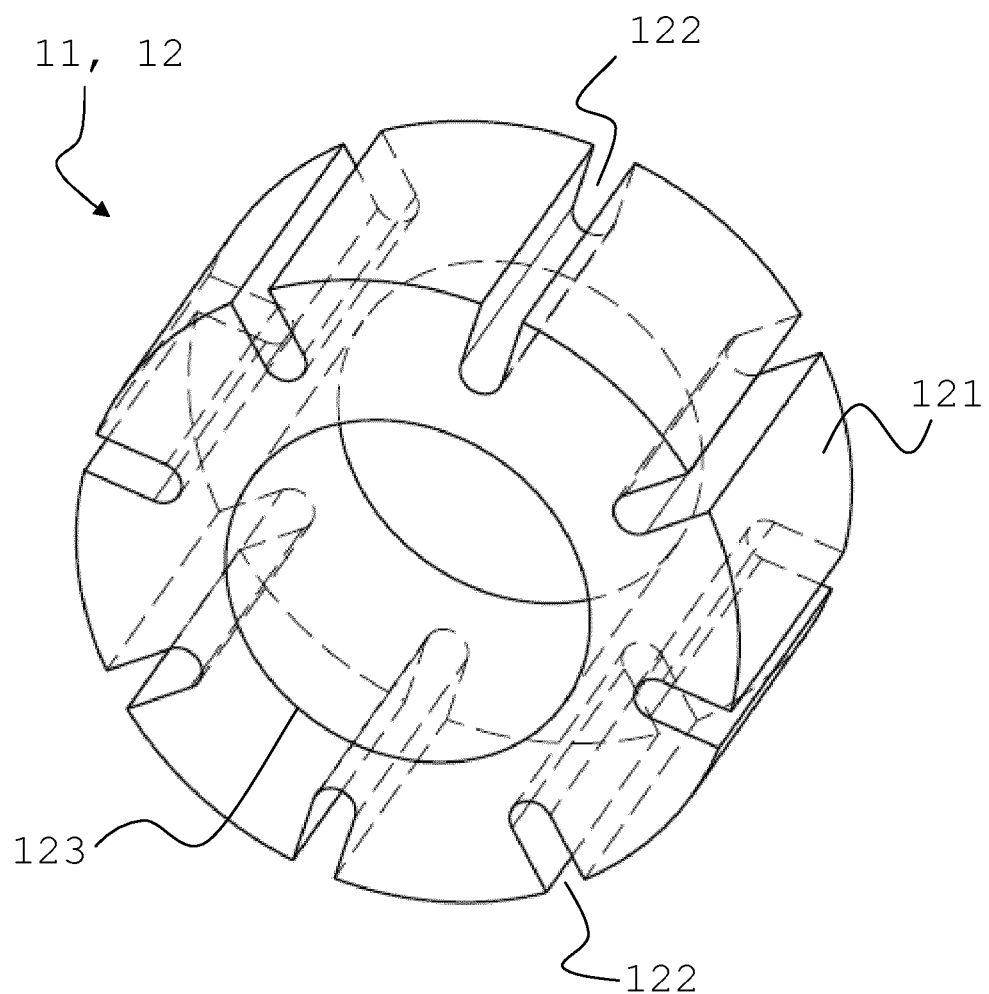
FIG. 2 represents a structural member of the force transducer of FIG. 1.

Members 11 and 12 are hence advantageously rigid and may assume any shape. Advantageously, as shown in FIG. 2, they comprise a cylindrical outer surface 121 provided with possibly axial grooves 122 in which the optical fibres fit and wherein they are secured. Other ways of attaching the optical fibres, such as by potting them in holes in the members, by clamping, etc. are possible as well.

The members 11, 12 can be made of any material suitable for the intended use, e.g. a biocompatible material: polymeric, metal or ceramic. They can be manufactured by conventional machining, laser machining, micro-injection, electrical discharge machining, chemical machining, rapid prototyping, extrusion, etc.

When in use in the configuration as depicted in FIG. 1, member 11 will be the most distal one, and can be arranged to be linked to a medical tool (such as needles, knives, etc.), on which the acting forces are to be measured. Member 12 will then be the most proximal one, and can be arranged to be linked to a connecting body, for providing connection to a proximal end of e.g. an endoscopic assembly.

Depending on the application, the members 11, 12 can present particular features, such as holes, notches, etc. in order to fulfil specific functions. By way of example, the members 11, 12 in FIGS. 1-2 are provided with coaxial through-holes 123 arranged for passage of a tube or other conduct between a proximal end and the medical tool (the distal end of the assembly). The tube can be used for the injection of a fluid and/or for passing cables.

According to the invention, optical fibres 13 extend between the members 11, 12 and are fixed to both of them. Fixing can be done with any means known in the art, such as a weld joint, adhesive, epoxy potting, clamp and screw, a clasp, etc. Optical fibres 13 advantageously further extend at the proximal side 124 of the proximal member 12, which can allow to connect the optical fibres 13 to a control unit for sending and receiving light through the fibres as is known in the art.

A plurality and possibly all of the optical fibres 13 are configured to provide a change in a detectable optical property responsive to a change in strain in the freely suspending part 131. Any provision or means 132 in or at an optical fibre which is able to transform the strain thereof in a detectable optical signal, hereinafter referred to as optical strain detection means, is eligible for being used in the present invention. By way of example, such optical strain detection means can be one, or a combination of Fibre Bragg gratings, Long-Period fibre gratings, Intrinsic Fabry-Pérot interferometers, Michelson interferometers, Brillouin scattering, Intensity interferometer. A plurality of such optical strain detection means can be provided on a single fibre, at a same or different location. In order to enhance the transducer output, different optical fibres can be provided with different above indicated means. Possibly, strain detection means can be configured to exploit structural slow/fast light, nonlinear phase shift enhancement, or chaotic propagation of light.

Advantageously, the force transducer 10 includes a redundancy in the detection of strain of the optical fibres. Therefore, force transducer 10 preferably comprises a number of optical fibres 13 equipped with a strain detection means 132, such that, for each degree of freedom for which transducer 10 is configured for measuring a force, at least two, advantageously at least three optical fibres 13 provide a response. Advantageously, for each degree of freedom for which transducer 10 is configured for measuring a force, force transducers according to the invention comprise more optical fibres 13 with strain detection means 132 than the minimal number technically required for performing a force measurement, advantageously at least one more, advantageously at, least two more. It will be convenient to note that some optical fibres 13 can be used for force measurements according to a plurality of degrees of freedom.

Therefore, each relative displacement between the two members 11 and 12 according to a degree of freedom, for which a force is to be measured, will advantageously cause a detectable change in at least two, preferably at least three, preferably at least four optical fibres 13. It can cause a detectable change in all the fibres.

Force transducers of the invention can be designed to perform force measurements according to both translational and rotational degrees of freedom. Advantageously, force transducers according to the invention are configured for at least performing force measurements in a direction along the common axis 14 (centreline) between the two structural members, corresponding to a translational degree of freedom along axis 14.

Possibly, though not necessarily, the optical fibres 13 are arranged parallel to the axial orientation of the transducer 10. They are advantageously disposed at regular intervals, such as at the vertices of an equilateral polygon.

The transducer's axial orientation corresponds to the common axis 14 of the two members 11, 12, which in a general case will correspond to the proximal-distal orientation.

By way of example, FIG. 1 shows force transducer 10 comprising eight parallel optical fibres 13, oriented along the axis 14 of transducer 10 and arranged regularly at the vertices of an octagon. At least part of these fibres 13, and advantageously all of them can comprise strain detection means 132 configured to provide a change in a detectable optical property responsive to strain of the freely suspending part of the fibre as indicated above.

Several types of optical fibres can be used in transducers according to the invention, such as single-mode and multi-mode silica and polymer optical fibres, polarization maintaining fibres, photonic crystal fibres, microstructured optical fibres or even chalcogenide optical fibres. The optical fibres can comprise a core and a possibly protective sheath as is known in the art.

As will be explained, it is possible that a connection between the two members 11 and 12 other than via the optical fibres 13 is present, such as ducts passing through the opening 123 of both members and attached thereto. Such a connection however should be sufficiently elastic, such that the rigidity of the link between members 11 and 12 along those degrees of freedom configured for force measurement is not substantially affected and remains mainly due to the optical fibres as indicated above.

Therefore, the length of the freely suspending part 131, the size and number of optical fibres to suspend between the members as well as their disposition should be selected in function of the transducer's specifications.

Advantageously, the length of the freely suspending part 131 (measured between the locations of attachment of the optical fibre to the members) is at least 1 mm, possibly at least 2 mm. Said length of the freely suspending part 131 is advantageously smaller than or equal to 15 mm, advantageously smaller than or equal to 10 mm, advantageously smaller than or equal to 8 mm. Advantageously, the optical fibres 13 have about a same length of free suspension between the structural members 11 and 12. Advantageously, the lengths of free suspension of the optical fibres 13 occur at a same location along the axis 14 of the transducer 10, i.e. there is advantageously no shift of optical fibres along that axis, such that the lever arm to the force is about the same for all the optical fibres.

Force transducers of the invention advantageously have overall dimensions which make them suitable for use in minimally invasive surgery.

Advantageously, the optical fibres 13 are not pre-tensioned.

Figure 9:
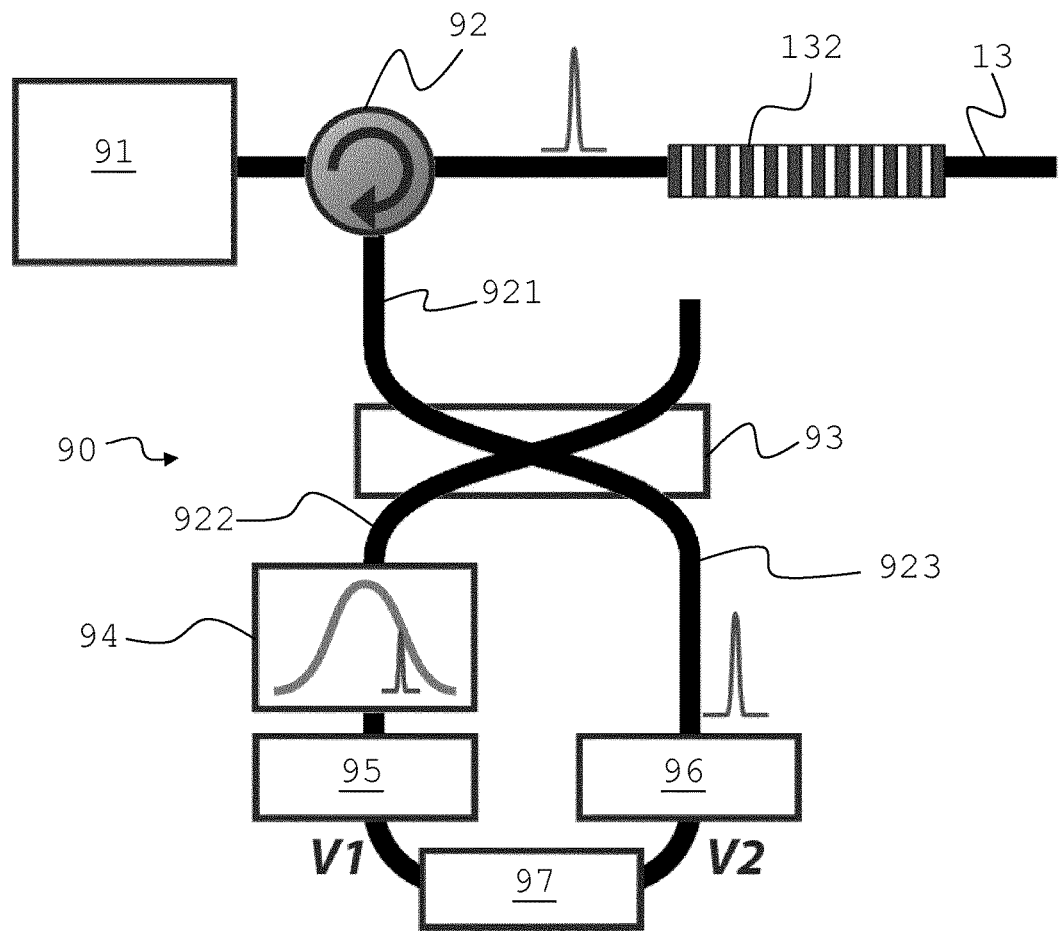
FIG. 9 represents a scheme for operating an optical fibre of a force transducer according to the invention.

A system 90 as represented in FIG. 9 can be used for operating the transducer and performing a measurement in the optical fibres. The scheme is given for one optical fibre 13 provided with an optical strain detection means 132, such as a fibre Bragg grating, but can easily be extrapolated for all the optical fibres of the transducer. The optical fibre 13 is connected to a light source 91 such as a laser, emitting light through the fibre, which is reflected in the Bragg grating 132. An output coupler 92 is arranged along the fibre path and deviates the reflected light beam 921. The deviated light beam 921 passes a beam splitter 93, splitting the beam 921 into two components. A first component 922 passes through a linear filter 94, which reduces the luminous intensity (amplitude depending linearly on the wavelength of beam 922). The second component 923 remains unfiltered and serves as a reference of the energy content of the beam 921. Both beams 922 and 923 subsequently pass through corresponding photo detectors 95 and 96 which output electric voltage signals V1 and V2 respectively being linear functions of the beam intensity. Voltage signals can subsequently be acquired by a data acquisition device 97 for further processing. The strain of fibre 13 will be proportional to the ratio V1/V2. It will be convenient to note that other systems can be used to measure the strain of fibre 13, as are known in the art.

Force transducers of the invention can incorporate a temperature compensation system. One or more additional optical fibres can be provided (not shown), which are only attached to one of the members (usually the proximalmost one), but not both. Hence, the additional optical fibres are not configured for being strained when the transducer experiences a force. The additional optical fibres can however be provided with same optical strain detection means, the outputs of which will change with temperature. This change in output can be used for temperature compensation of the outputs provided by the strained fibres. Alternatively, one or more optical fibres 13 used for force measurement can be provided with an optical strain detection means at locations which are not strained when a force is acting on the transducer, such as at or beyond (i.e. proximal of) a proximal end 124 of the proximalmost member 12.

Measurements with force transducers according to the invention can be performed by taking the following theoretical considerations into account. The force acting on the (members of the) transducer is transmitted to the optical fibres, which as a result are strained in axial direction. Basically, for one fibre in traction, the following relations can be set out:

$$Fn = \varepsilon SE = \frac{\Delta L}{L} SE$$

with Fn the normal force applied at the extremity of a portion of a fibre, S the cross section of the optical fibre, E the Young's modulus of the optical fibre, ε the strain of the fibre, L the length of free suspension of the optical fibre and ΔL the change in length.

The stiffness of the optical fibre is defined by:

$$k = \frac{Fn}{\Delta L} = \frac{SE}{L}.$$

Such stiffness is to be considered according to each degree of freedom of the force transducer. Each one can be estimated from a complex set of such basic relations, considering the number of optical fibres, their disposition, etc.

The force according to each degree of freedom can be computed from the stresses induced in each optical fibre. These stresses can be calculated based on a change in the optical property which is responsive to the strain corresponding to the stress. By way of example, for a fibre Bragg grating provided in the freely suspending part of the optical fibre, the elongation of the optical fibre is proportional to a wavelength shift: $\Delta L = \kappa \Delta \lambda$, with κ a constant ratio and Δλ the wavelength shift. The normal force exerted on the fibre is thus: $Fn = k\kappa\Delta\lambda$.

The number of fibres configured to provide a change in an optical property responsive to a strain in the freely suspending part (referred to as the sensing fibres) is at least equal to, and advantageously larger than the number of forces and bending moments to compute. It will be advantageous to provide an excess number of sensing fibres, which provides a redundancy of information and leads to a more stable and more accurate measurement.

Alternatively, or in addition, an excess number of optical fibres is advantageously used to increase the stiffness of the link between the members 11, 12.

Considering all six degrees of freedom, the set of forces acting on the transducer can be expressed as three forces according to three orthogonal axes (with axis z oriented in the transducer's axial direction and two perpendicular axes x and y) and three bending moments by making a linear combination of the normal forces exerted on each fibre. Considering a configuration of n fibres, the forces are recovered by the following equation:

$$\begin{pmatrix} F_x \\ F_y \\ F_z \\ M_x \\ M_y \\ M_z \end{pmatrix} = \begin{pmatrix} a_{x1} & \ldots & a_{xi} & \ldots & a_{xn} \\ a_{y1} & \ldots & a_{yi} & \ldots & a_{yn} \\ a_{z1} & \ldots & a_{zi} & \ldots & a_{zn} \\ b_{x1} & \ldots & b_{xi} & \ldots & b_{xn} \\ b_{y1} & \ldots & b_{yi} & \ldots & b_{yn} \\ b_{z1} & \ldots & b_{zi} & \ldots & b_{zn} \end{pmatrix} \begin{pmatrix} k_1\kappa_1\Delta\lambda_1 \\ \vdots \\ k_i\kappa_i\Delta\lambda_i \\ \vdots \\ k_n\kappa_n\Delta\lambda_n \end{pmatrix}$$

Coefficients $a_{ij}$ and $b_{ij}$ can be estimated from analytical law derived from structural mechanics or by finite element method. An experimental calibration can be used to determine the coefficients.

Transducers according to the invention are advantageously used in assemblies designed to provide a feedback of the force (or anything else that may be relevant, such as displacement) to the surgeon. This can be accomplished in numerous ways, including but not limited to visually, by a light or acoustic signal, by a haptic sensation reconstructing the force, etc. The force measured by force transducers of the invention can be pre-processed, for example by providing filters, amplifiers, etc. as is known in the art.

The interpretation of the force measured, in particular of a sudden change in force, such as when a needle pierces a tissue, can be improved by coupling the transducer according to the invention to a position encoder which e.g. measures the relative motion between the catheter to which the transducer is fixed, and the endoscope or other device relative to which the catheter is moving. Referring to the above case, a needle piercing a tissue can be identified by the fact that the sudden change in force level is accompanied by a constant position as read by a position encoder. Conversely, a shock can be identified by a sudden change in force level which is accompanied by a position change. Therefore, the provision of a position encoder allows for discriminating between different situations.

It is also possible to use the transducer output and position information of an encoder in an automatic feedback loop in order to automatically adjust the position of a catheter relative to an endoscope or any other reference. A control unit equipped with a man-machine interface enabling a surgeon to control the (motorized) advancement of the catheter can include a force feedback loop in the motion control of the catheter.

An example of a medical application in which force transducers according to the invention can be used is the insertion of a liquid polymer in the muscularis externa of the stomach near the cardia to reduce gastric reflux. Force transducers according to the present invention can be used to measure sudden changes in force level so as to detect the transition between several tissue layers during the insertion of a needle, such that it can be ascertained that the needle arrives in the correct tissue layer.

Figure 3:
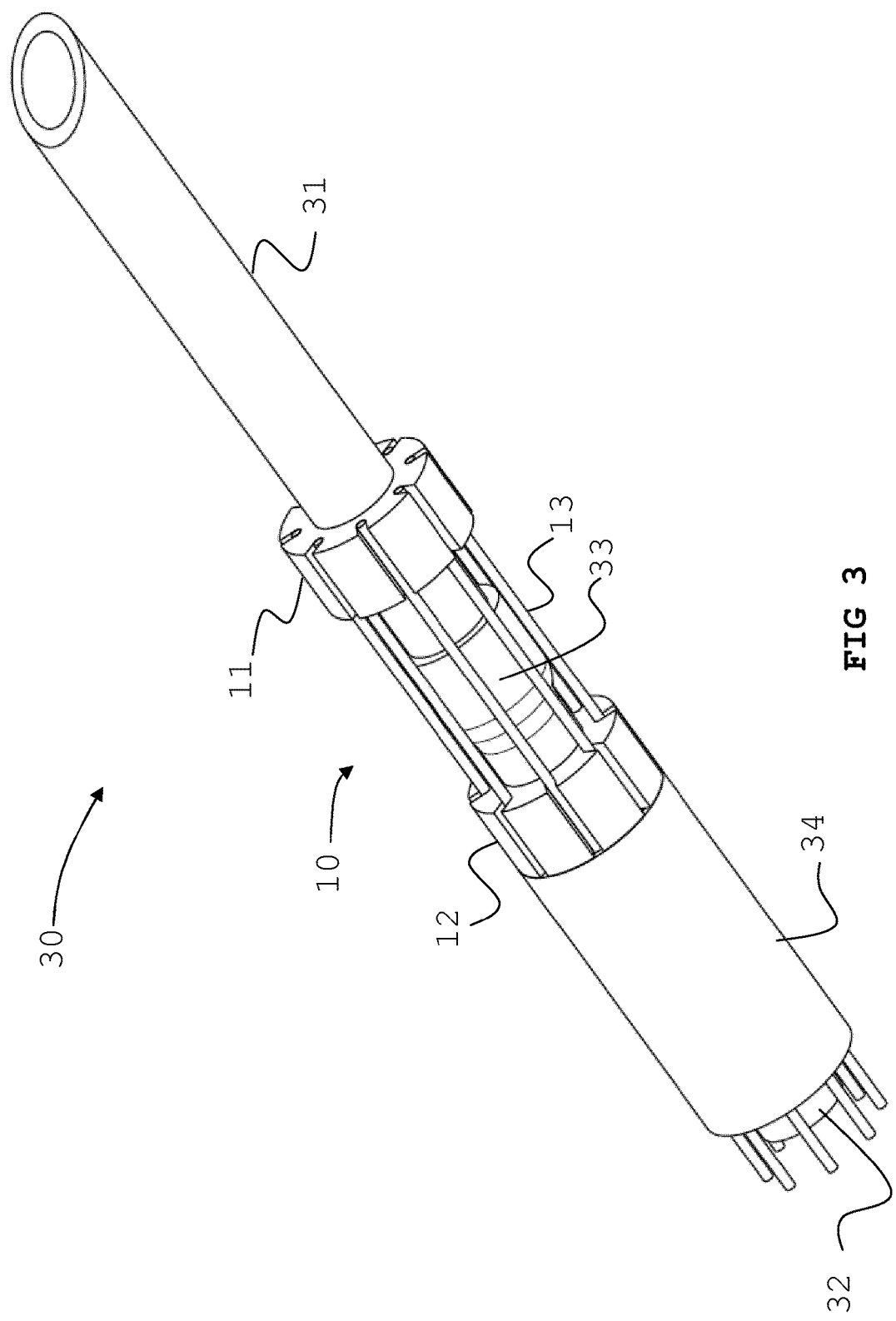
FIG. 3 represents a perspective view of an assembly of a hollow needle at the end of, a fluid delivery catheter to which the force transducer of FIG. 1 is mounted.

An implementation embodiment of the force transducer 10 is shown in FIG. 3, which depicts an assembly 30 comprising a hollow needle 31 linked to a fluid delivery tube 32. Assembly 30 can be configured for use in endoscopic microsurgery, such as for injecting a liquid in the muscularis externa as described above.

Another possible application in which force transducers according to the invention can be used is with biopsy needles (aspiration needles). Providing a force transducer according to the invention between duct and needle allows to differentiate between healthy tissue, metastasis and tumour.

Yet another possible application is endoluminal submucosal dissection (ESD), in which a tumour located in a mucosal plane is dissected. The dissection is carried out by separating the mucosal plane from the underlying muscular plane by sectioning the submucosal tissue. After having located the tumour, a marking is applied around the tumour site (in healthy tissue). At the marking sites, physiological serum or hyaluronic acid is injected, such as by a needle assembly 30, in the submucosal tissue. This creates a liquid bag in the submucosal tissue, lifting and isolating the tumour site from the muscular plane. This allows to perform a clear-cut section around the tumour site without compromising the muscular plane. Force transducers 10 according to the present invention can be used in dissecting assemblies for locating the correct tissue when performing the dissection. This is possible, since the different tissue layers have different elasticity, so that force level changes occur at the interfaces between tissue layers.

In needle assemblies 30, the force transducer 10 is mounted at the interface between the needle 31 and the fluid delivery tube 32. Distal member 11 is secured to the needle 31. In the present example, distal member 11 comprises a central through hole 123 which snugly fits around the needle 31.

Proximal member 12 is secured to the distal end of the fluid delivery tube 32. A central through hole 123 is likewise provided in the proximal member 12 for fitting around the tube 32. An elastic connecting piece 33 is provided between the needle 31 and the tube 32 in order to guarantee water tightness. Connecting piece 33 is arranged between the distal and proximal members 11 and 12 respectively. As can be seen from FIG. 3, the optical fibres 13 are arranged around connecting piece 33.

Figure 10:
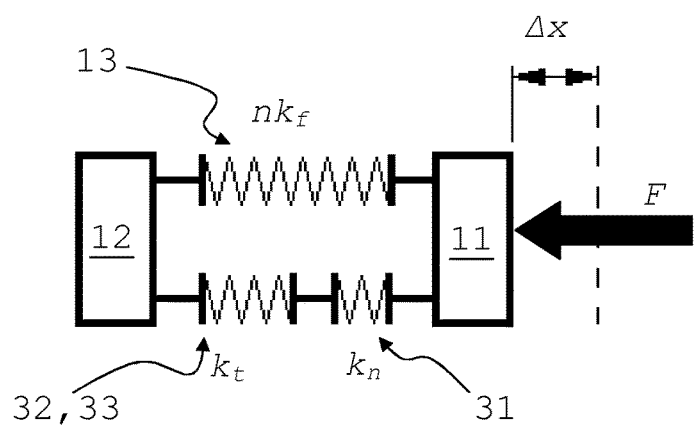
FIG. 10 represents a scheme for evaluating the stiffness of the link between structural members for the case of FIG. 3.

According to the invention, the rigidity (stiffness) of the link between the members 11 and 12 is mainly due to the optical fibres 13, which are secured to both members 11 and 12. Therefore, connecting piece 33 and tube 32 are made suitably elastic in order not to interfere with the strain measurements effected on the optical fibres. An evaluation of the contribution of elastic connecting piece 33 to the stiffness of the link between members 11 and 12 for an axial load can be made as follows with reference to FIG. 10. The link between members 11 and 12 is formed by the assembly of optical fibres 13 on the one hand and the connection between tube 32, elastic connecting piece 33 and needle 31 on the other. For small deformations, both link types can be modelled as two linear spring systems according to the equation $F=k \Delta x$, with F the force acting on the system, k the stiffness and $\Delta x$ the displacement. For an assembly of n optical fibres 13 which contribute in parallel to the stiffness of the link, the resulting equation is: $F=nk_f \Delta x$, with n the number of optical fibres and $k_f$ the stiffness of one optical fibre. Conversely, in the assembly of needle 31, tube 32 and connecting piece 33, the spring systems of the different constituents are arranged in series as shown in FIG. 10. Let's consider for the sake of simplicity the case wherein the connecting piece 33 is integral with and hence made of a same material as tube 32 and has a same cross sectional area. Hence the two can be considered as one single item with the portion between member 12 and the needle 31 having, a resulting stiffness $k_t$. It is known that the resulting stiffness $k_{nt}$ of a series of two springs can be written as:

$$k_{nt} = \frac{k_n k_t}{k_n + k_t}$$

with stiffness $k_n$ being the stiffness of the needle portion 31 between member 11 and connecting piece 33. It is recalled that the stiffness k of a structure can be calculated based on its geometry and Young's modulus to be $k=SE/L$ with S the cross sectional area, E Young's modulus and L the length of the structure. In the assumption that needle 31 and tube 32 have identical cross sectional area S and that the needle is made of metal. (e.g. stainless steel), whereas the tube is made of a resilient material, such as polyurethane, the needle material will have a Young's modulus being more than thousand times larger compared to the tube's material. In such case, $k_n \gg k_t$ and $k_{nt}$ can be approximated by $k_t$.

Referring to FIG. 10, the two spring systems of optical fibres 13 and needle 31, tube 32 and connecting piece 33 act in parallel to withstand force F acting on needle 31 and hence on member 11 and both experience a same displacement $\Delta x$ between members 11 and 12 due to force F. The overall stiffness of the link between members 11 and 12 is hence $K=nk_f+k_{nt}$ and the contribution of the optical fibres to the overall stiffness of the link amounts to $\rho_f=nk_f/K$.

By way of example, let us consider members 11 and 12 spaced 3 mm apart and having internal bores of 1.1 mm diameter to which the needle 31 and the tube 32 are attached. Connecting piece 33 is integral with tube 32. Needle 31 projects 2 mm in the gap between the structural members 11 and 12; the remainder being bridged by the tube 32 (and connecting piece 33). Both needle 31 and tube 32 are hollow with inner bore of 0.8 mm diameter. The needle is made of stainless steel, whereas the tube and connecting piece are made of polyurethane (E=100 MPa). Therefore, the stiffness $k_{nt}$ can be approximated by the stiffness of the tube portion $k_t$. A total of eight optical fibres are arranged around members 11 and 12. The stiffness of one optical fibre 13 can be calculated to be about $k_f=1600$ N/mm. Tube 32 has a cross sectional area (solid material) S=1.79 mm². Based on the above data one obtains:

$$k_{nt} \approx k_t = 179 \text{ N/mm}.$$

The overall stiffness of the link is $K=8k_f+k_{nt}=12\,979$ N/mm. The contribution of the optical fibres to the overall stiffness of the link hence amounts to:

$$\rho_f = 8k_f/K = 0.986, \text{ or } 98.6\%.$$

Proximally of the proximal member 12, the optical fibres 13 further extend towards a measurement acquisition system 90 as depicted in FIG. 9. A protective sheath 34 which wraps tube 32 and optical fibres 13 can be provided proximally of the proximal member 12.

An advantage of transducers according to the invention is that the measurements are not influenced by bodily fluids, so that in principle the force transducer need not be protected from the environment. However, it will be convenient to envelope the force transducer 10 in a flexible bag, in order to prevent that any protrusions might harm the body.

In a typical application, the force range in which transducers of the invention are configured to measure lies between about 0 N to about 10 N.

Figure 4:
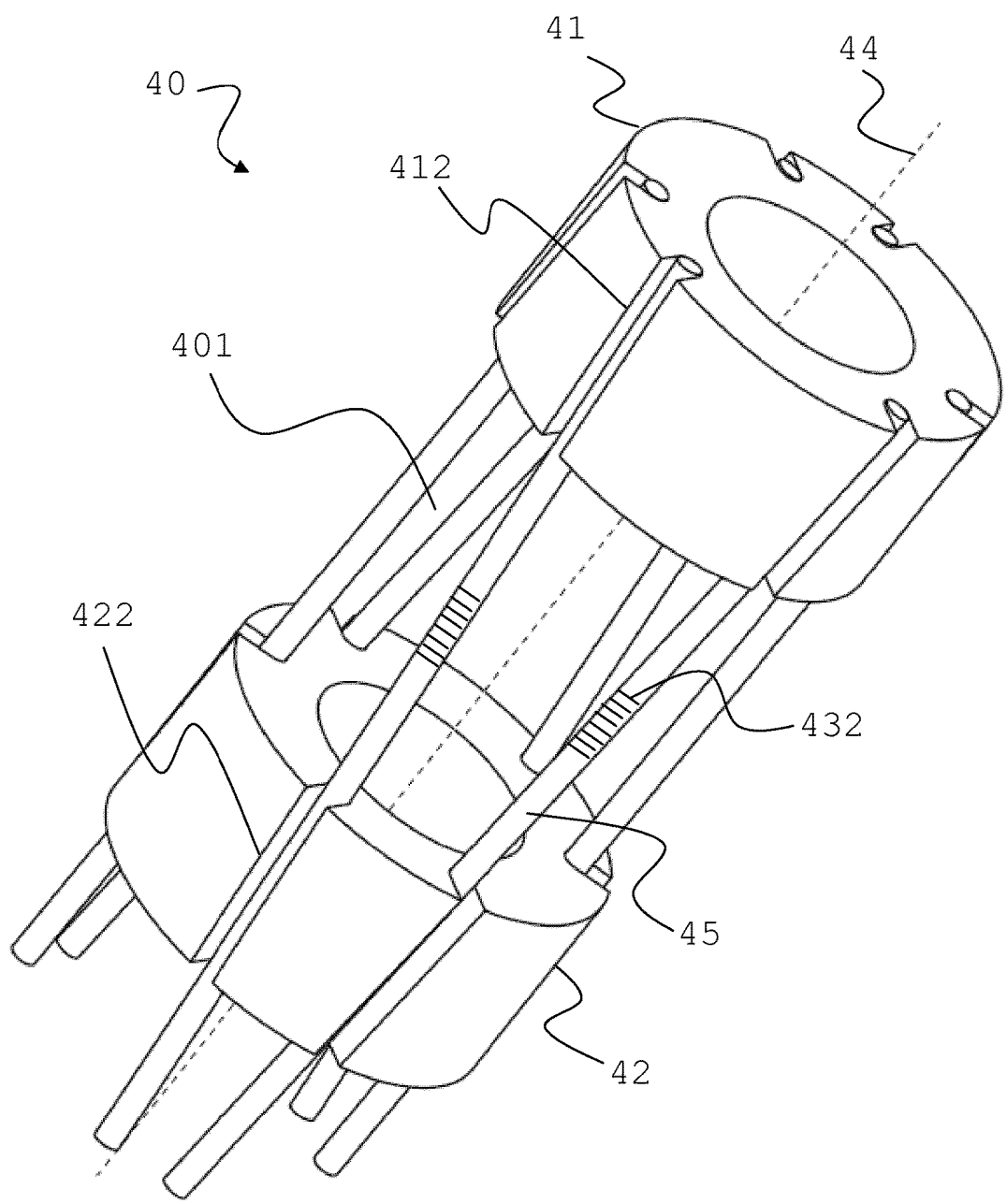
FIG. 4 represents a perspective view of another embodiment of a force transducer according to the invention.

FIG. 4 represents another force transducer 40 according to the invention. Unlike the force transducer 10, wherein all the optical fibres 13 are parallel in axial direction, force transducer 40 comprises optical fibres 45 arranged obliquely to the axis 44 of the transducer. The structural members 41 and 42 are spaced apart by a gap 401 and the optical fibres 45 bridge the gap 401 and are secured to both structural members 41 and 42. Optical fibres 45 can be provided with optical strain detection means 432 arranged between the members 41 and 42.

An advantage of obliquely arranged optical fibres 45 is that also forces acting laterally on the transducer 40 (i.e. transverse to the proximal-distal direction) can be measured, which is not always (or at least less) the case when only axially parallel fibres are used. The oblique orientation of the fibres allows lateral forces to induce a normal strain in the fibres. The angle between the axis 44 and the oblique fibres (in projection on a plane parallel to axis 44) is advantageously at least 10°, advantageously at least 15°. Said angle is advantageously at most 45°, advantageously at most 40°.

Force transducers of the invention can comprise a combination of obliquely arranged optical fibres and parallel arranged optical fibres.

The grooves 412, 422 in structural members 41 respectively 42, which accept the optical fibres 45, run parallel and are aligned with the oblique fibres 45 and are hence oriented obliquely as well.

Another possibility for effectively measuring lateral forces, but without requiring having to orient the optical fibres obliquely relative to the axis of the transducer is represented in FIG. 5. Force transducer 50 comprises structural members 11 and 12 as with force transducer 10 represented in FIG. 1. Structural member 11 is the distalmost one and is configured for attachment to a distal medical tool. Structural member 12 is the proximalmost one and is configured for attachment to a proximal connecting structure, such as an endoluminal tube. Optical fibres 13 extend continuously to span the distance between the structural members 11 and 12 and are secured to both of them, e.g. in grooves 122.

Force transducer 50 differs from transducer 10 in that a third structural member 55 is interposed between the two other structural members 11 and 12. Structural member 55 may have same shape and structure as either one or both the structural members 11 and 12. The optical fibres 13 are secured to the third structural member 55 as well, such as in the grooves 552. The third structural member 55 together with the optical fibres 13 therefore advantageously forms a freely suspending structure between the two outer structural members 11 and 12, meaning that the third member 55 is advantageously neither attached to the medical tool, nor to the proximal structure.

Member 55 is advantageously attached to the optical fibres 13 only. It divides the span of optical fibres 13 between members 11 and 12 in two parts, notably a distal part 56 and a proximal part 57. In both parts 56 and 57, the optical fibres 13 are freely suspended.

Figure 5A:
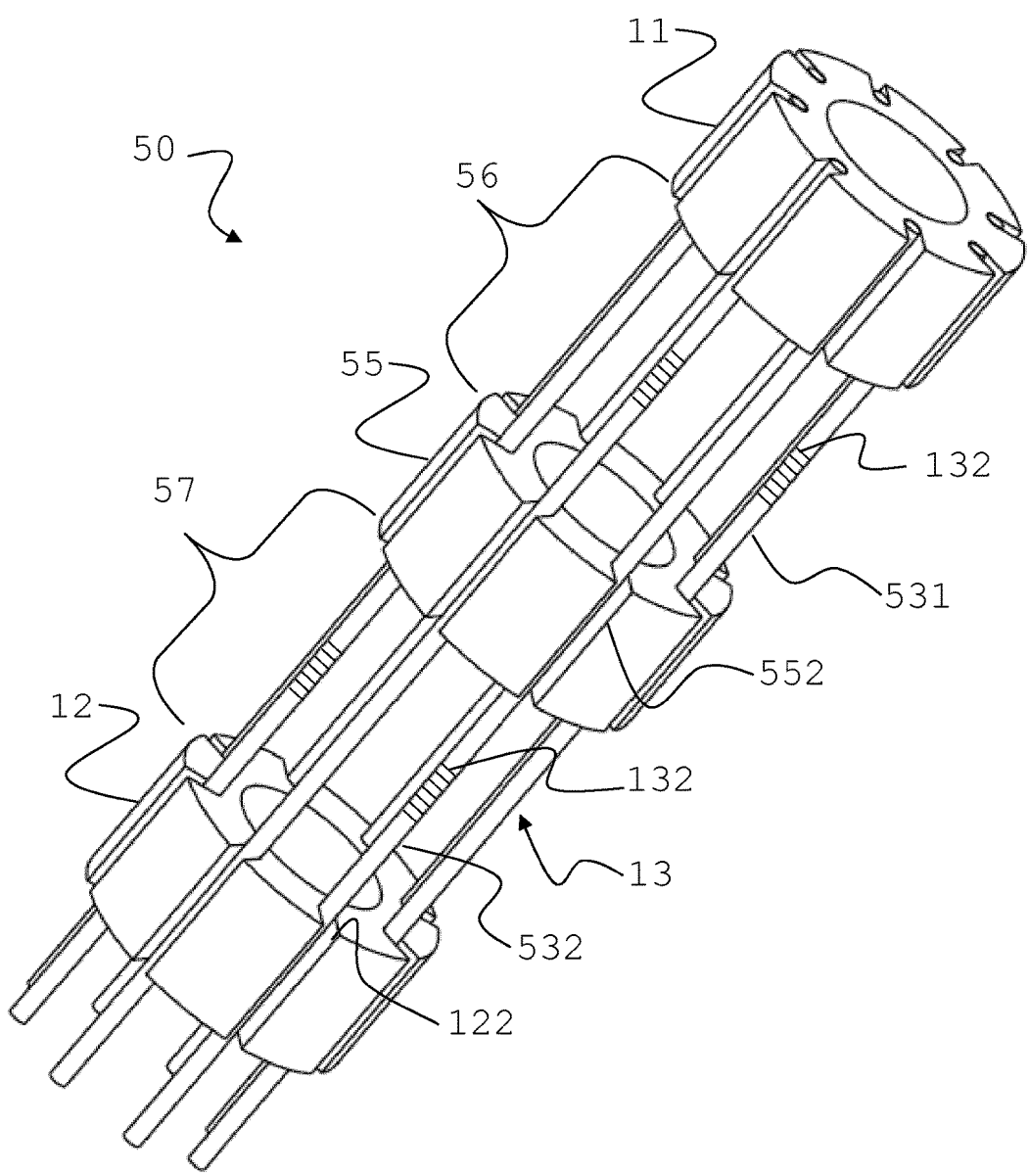
FIG. 5A represents a perspective view of yet another embodiment of a force transducer according to the invention.

The optical fibres 13 are provided with optical strain detection means 132, configured for measuring strain distinctly in both parts 56 and 57. In the example of FIG. 5A, the optical fibres 13 are divided in first optical fibres 531, which are provided with optical strain detection means 132 in or along the distal part 56 (but not the proximal part 57), and in second optical fibres 532, which are provided with optical strain detection means 132 in or along the proximal part 57 (but not the distal part 56). In such case it is also not required to have all optical fibres 13 secured to all three structural members 11, 12 and 55. The first optical fibres 531 may be secured to the two distalmost structural members 11 and 55, but not to the proximal member 12. Similarly, the second optical fibres 532 may be secured to the two proximalmost structural members 12 and 55, but not to the distal member 11. The second optical fibres may even not extend distally from the interposed structural member 55. It may however be advantageous to have about equal rigidity in both the distal and proximal parts 56 and 57, so that the number of optical fibres 13 secured to the two distalmost structural members 11 and 55 equals the number of optical fibres 13 secured to the two proximalmost structural members 12 and 55. Hence, it is advantageous that all the optical fibres 13 are secured to all the three structural members 11, 12, and 55.

In a yet alternative embodiment, optical fibres 13 may be provided with optical strain detection means 132 in both the distal and proximal parts 56 and 57. Such a configuration will however require signal differentiation and leads to a somewhat more complex system. In this case, the optical fibres need be secured to all three structural members 11, 12 and 55.

It will be convenient to note that in the three-member examples, the optical fibres 13 are advantageously oriented parallel with the transducer's axis.

Figure 5B:
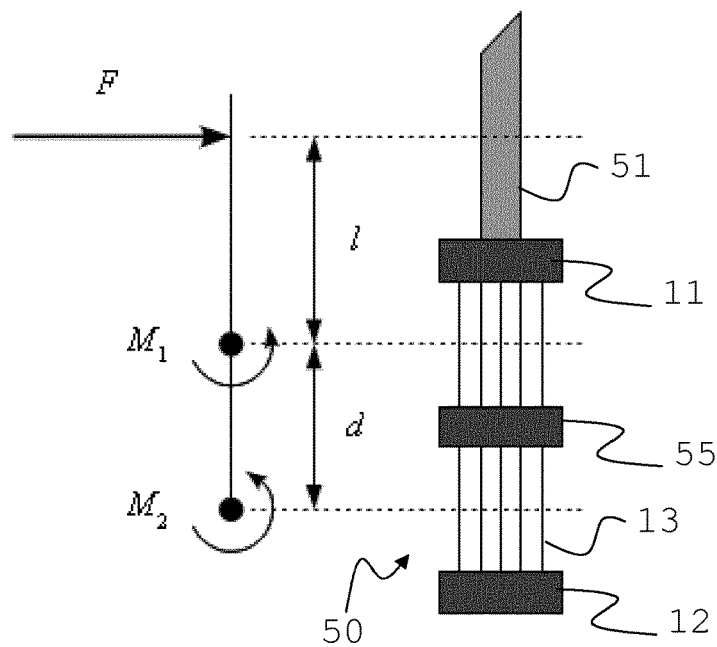
FIG. 5B represents schematically the force exerted on an extremity of the transducer (the tool) and the bending moments occurring within the force transducer of FIG. 5A.

The principle of operation of force transducer 50 is now explained with the aid of FIG. 5B, which schematically represents force transducer 50 on which a medical tool, such as a needle 51 is mounted. A lateral force F acting on needle 51 can be calculated based on the strain measured in the optical fibres 13 in both parts 56 and 57. Considering the distal part 56 and the proximal part 57 of optical fibres to be unitary structures, such as beams, then a bending moment diagram along the transducer can be constructed according to the theory of elasticity. The bending moment $M_1$ at the location of the optical strain detection means 132 in the distal part 56 of the optical fibres 13 and the bending moment $M_2$ at the location of the optical strain detection means in the proximal part 57 of the optical fibres 13 relate to F in proportion to the lever arms I and I+d between the point of incidence of F and the location of the optical strain detection means 132 in the distal and the proximal parts 56 and 57 respectively. $M_1$ and $M_2$ can be calculated based on the strain (differences) measured in the different optical fibres 13, in both suspending parts 56 and 57. When one considers F to be a resultant force acting on a predetermined location along the medical tool (e.g. at halfway of its length), F can be calculated with the following formulae:

$$M_1 = Fl$$

$$M_2 = F(l+d)$$

from which it can be derived that.

$$M_2 - M_1 = Fd$$

$$F = \frac{M_2 - M_1}{d}$$

Figure 6:
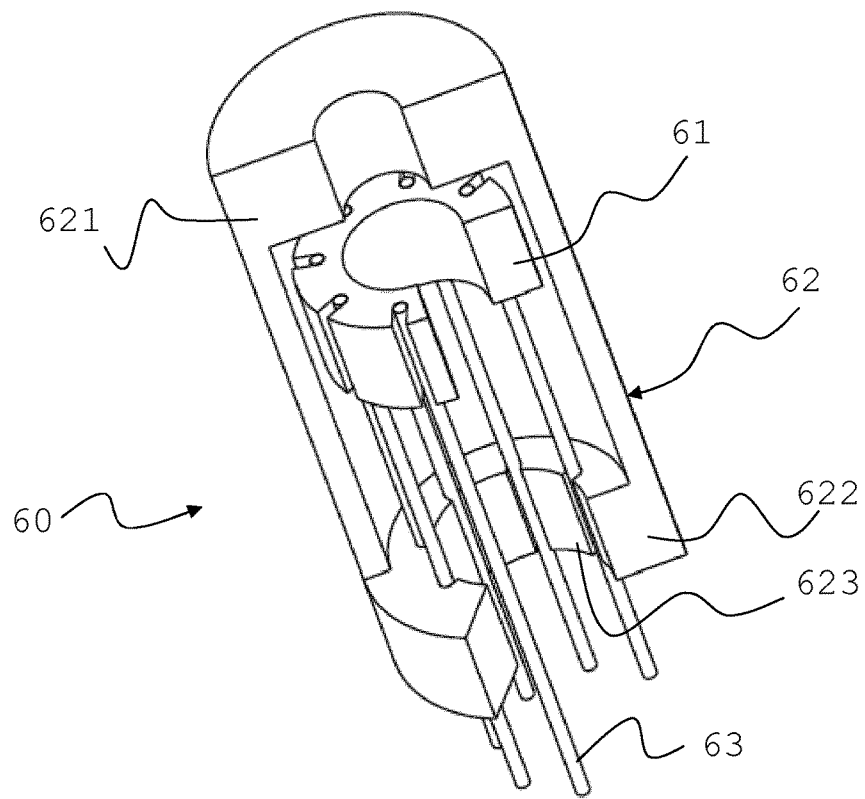
FIG. 6 represents a perspective view with partial cut-out of yet another embodiment of a force transducer according to the invention.

Yet another force transducer 60 according to the invention is represented in FIG. 6, wherein the proximal member 62 comprises a proximal end 622 and a hollow cylinder-like or tubular projection 621 which extends distally from the proximal end 622 to wrap the distal member 61, so that the distal member 61 is located inside the hollow projection 621.

Proximal member 62 can furthermore comprise a through hole 623 by which the distal member 61 can be reached from a proximal side.

Optical fibres 63 extend between the distal member 61 and the proximal end 622 of the proximal member 62 and are secured thereto. With such an embodiment, a medical tool can be fixed at a distal end of projection 621 of proximal member 62, and a catheter or other linking device can be fixed to the distal member 61 while freely passing through the hole 623, resulting in the optical fibres being subjected to traction instead of compression. This has the advantage that there is no risk of buckling of the fibres when the force would be too high. It is hence a more robust force transducer than the ones previously described.

Another advantage of transducer 60 is that the distal end of the optical fibres 63, between the distal member 61 and the proximal end 622 of proximal member 62 are protected by the cylinder-like projection 621.

The optical fibres in force transducers according to the invention are therefore disposed such that when a force to be measured is acting on the transducer, the optical fibres do not substantially bend or deflect. In other words, the optical fibres for force measurement are advantageously so disposed that they are only loaded under traction for forces acting along the degrees of freedom for which the transducer is configured for measurement.

Figure 7:
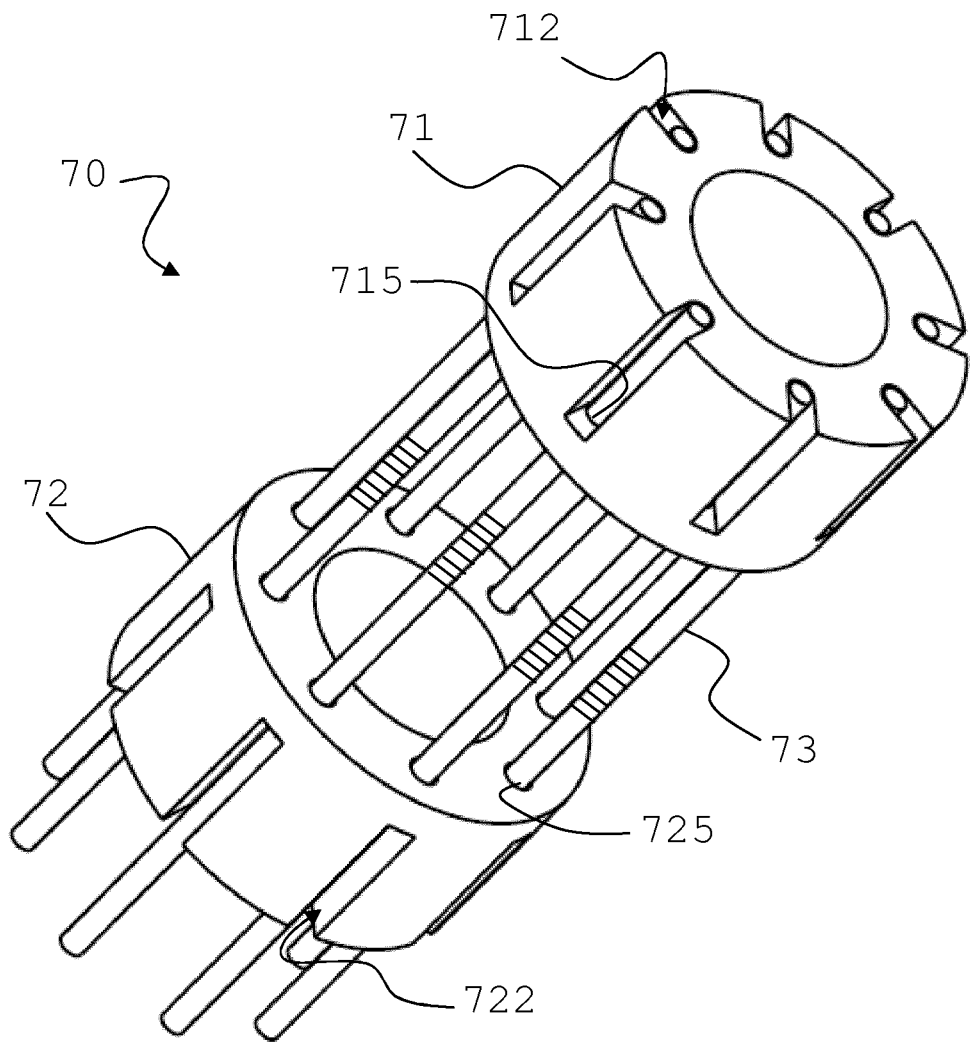
FIG. 7 represents a perspective view of a force transducer according to the invention having a slight constructional modification compared to the transducer of FIG. 1.

The force transducer 70 depicted in FIG. 7 comprises a slight constructional modification compared to the transducer 10 of FIG. 1. The structural members 71 and 72 comprise likewise axial grooves 712, respectively 722 for accepting the optical fibres 73. However, grooves 712, 722 terminate at either or both ends in holes 715, respectively 725, through which the optical fibres 73 pass. Holes 715, 725 advantageously extend through the corresponding member 71, 72 and are aligned with the grooves 712, 722. This solution allows for easily keeping the optical fibres in place during assembly to the structural members 71, 72, without requiring any clamping tool. Indeed, for assembling force transducer 70, one inserts the optical fibres through holes 725 and 715, such that the optical fibres extend along the grooves 722, 712. Adhesive is then applied in the grooves to secure the optical fibres to the structural members. The adhesive is then left to cure. Holes 715 and 725 prevent that the optical fibres would slip out of the grooves.

In force transducers according to the invention, advantageously, any one or both the proximal and distal members can comprise a mechanical limit in order to limit relative displacement between the two members and thereby protect the optical fibres in case of extreme load or misuse. The mechanical limit can be formed of a projection from one member towards the other one, and spaced apart from the latter under normal circumstances to only engage the latter in case of an excess of relative displacement.

Figure 8A:
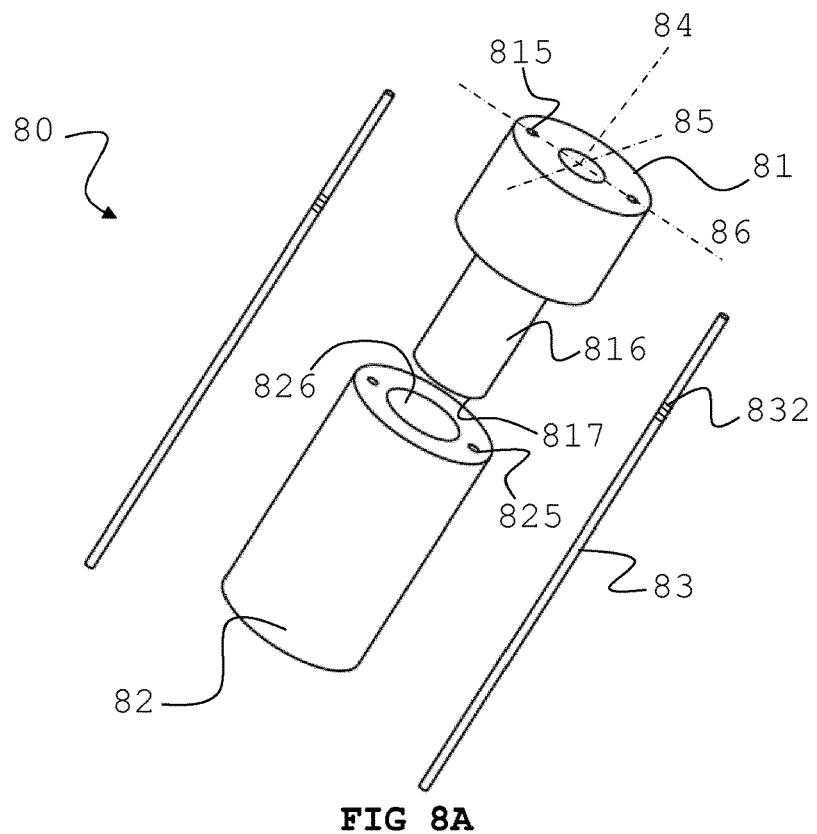
FIG. 8A represents an exploded view of another embodiment of a force transducer according to the invention.
Figure 8B:
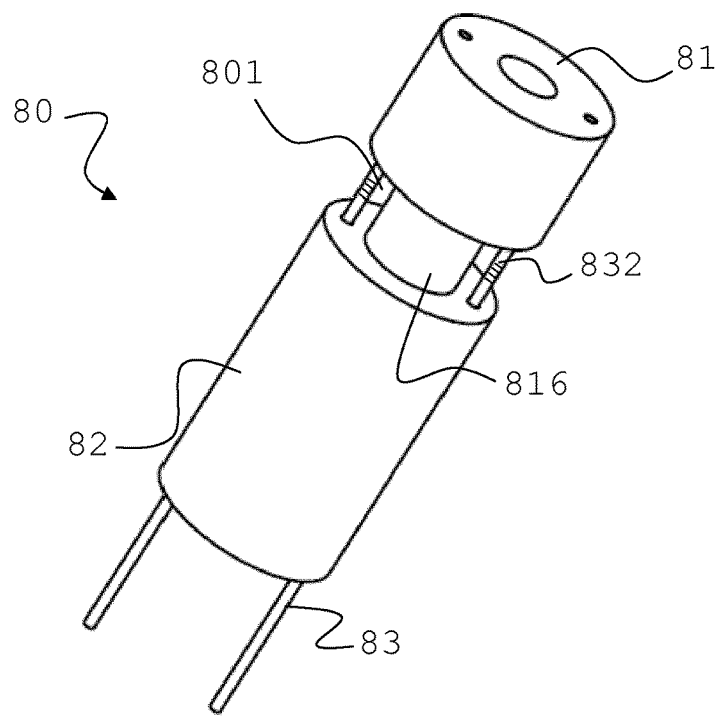
FIG. 8B represents a perspective view of the assembled force transducer of FIG. 7.

An example of a force transducer of the above kind is represented in FIGS. 8A-B. Force transducer 80 comprises only two optical fibres 83 which extend between the two structural members 81 and 82 and which are provided with optical strain detection means 832 along the freely suspending parts extending between the members 81, 82. The optical fibres 83 are secured in holes 815, 825 extending through the structural members 81, respectively 82. With only two optical fibres 83, force transducer 80 would be able to measure forces or force components acting only along axial direction 84 and about axis 85.

In order to reduce risk of buckling of the optical fibres 83 when subjected to forces acting along or about axes 85 and 86, a mechanical guide is provided between the structural members as follows. One of the two structural members 81, 82 of force transducer 80 (the distalmost one 81 in the example of FIGS. 8A-B) comprises a projection 816 extending towards the other member (the proximalmost one 82), the latter one being provided with a hole 826 accepting projection 816. Projection 816 and hole 826 are advantageously arranged in between the holes 815, 825 accepting the optical fibres. The hole 826 has a depth such that, when the transducer is assembled, projection 816 does not extend until the bottom of hole 826, but the projecting end 817 of projection 816 remains slightly elevated from the bottom of hole 826. The clearance between projecting end 817 and the bottom of hole 826 can be just enough to provide a mechanical limit for preventing buckling of the optical fibres 83 when a compressive force along axis 84 becomes excessive.

Alternatively or in addition, the size of hole 826 can be chosen such that projection 816 fits in sliding engagement. It is then obtained that the two members 81, 0.82 are allowed to displace relative to each other along axis 84, while degrees of freedom along or about axes 85 and 86 are suppressed. Furthermore, the cross-section of projection 816 and hole 826 can be made non-circular, which would also prevent any rotation about axis 84. In the present case, the optical fibres would be configured to measure forces acting along axis 84 only, since relative displacement between the members about axis 85 is constrained by the sliding engagement between projection 816 and hole 826.

It will be convenient to note that also in the example embodiment of FIG. 8 A-B, the structural members 81 and 82 are spaced apart all over their (overlapping) cross-sectional area, thus both in the gap 801 between the members, which is bridged by the optical fibres 83, and in the clearance between the projection 816 and hole 826.

The invention claimed is:

1. A force transducer comprising two structural members spaced apart to define a gap extending from one of the two structural members to the other one of the two structural members being linked to each other, and a plurality of optical fibres fixed to the two structural members, the plurality of optical fibres being freely suspended all along the gap, at least two of the plurality of optical fibres being each configured to provide a change in a detectable optical property responsive to a change in relative position between the two structural members in one or more predetermined degrees of freedom;

each of said plurality of optical fibres is fixed to each of the two structural members and continuous between the two structural members to link the two structural members to each other, and wherein the plurality of optical fibres are substantially the only structure forming a link between the two structural members, such that the number, disposition, sizes and lengths of free suspension of the plurality of optical fibres define substantially the stiffness of the link between the two structural members in the one or more predetermined degrees of freedom, which stiffness is mainly determined by the plurality of optical fibres;

wherein at least two of the plurality of optical fibres are spaced apart from one another all along the gap.

2. The force transducer of claim 1, wherein the one or more predetermined degrees of freedom comprise at least a translational degree of freedom along a common axis of the structural members.

3. The force transducer of claim 1, wherein the plurality of optical fibres are not pre-tensioned between the two structural members.

4. The force transducer of claim 1, wherein at least part of said plurality of optical fibres are parallel to one another and parallel to a common axis between the two structural members, at least along the length of free suspension.

5. The force transducer of claim 1, wherein the two structural members are aligned along a common axis, the two structural members being located at different positions along the common axis, wherein a first portion of said plurality of optical fibres extends parallel to the common axis along the gap, and wherein a second portion of said plurality of optical fibres extends obliquely to the common axis along the gap under an angle of at least 10° relative to the common axis, wherein at least one optical fibre of the first portion and at least one optical fibre of the second portion are configured to provide a change in a detectable optical property responsive to a change in relative position between the two structural members.

6. The force transducer of claim 1, comprising a third structural member aligned with and spaced apart from the two structural members to form a consecutive arrangement defining gaps between the three structural members, wherein a first group of the optical fibres are secured to first consecutive ones of the three structural members, are freely suspended in the gap between the first consecutive ones of the three structural members and are configured to provide a change in a detectable optical property responsive to a change in relative position between the first consecutive structural members in one or more predetermined degrees of freedom and wherein a second group of the optical fibres are secured to second consecutive ones of the three structural members, one of which being different from the first consecutive ones, are freely suspended in the gap between the second consecutive ones of the three structural members and are configured to provide a change in a detectable optical property responsive to a change in relative position between the second consecutive ones of the three structural members in the one or more predetermined degrees of freedom, and wherein the optical fibres are substantially the only structure forming a link between the three structural members, such that the number, disposition, sizes and lengths of free suspension of the optical fibres define substantially the stiffness of the link between the three structural members in the one or more predetermined degrees of freedom, which stiffness is at least 95% determined by the plurality of optical fibres.

7. The force transducer of claim 1, wherein the plurality of optical fibres are freely suspended over a length falling in the range between 1 mm and 15 mm.

8. The force transducer of claim 1, wherein at least part of the plurality of optical fibres are provided with fibre Bragg gratings between the two members, the Bragg gratings configured to influence the detectable optical property in response to a change in relative position between the two members.

9. The force transducer of claim 1, comprising a mechanical limit for limiting relative displacement of the two members in at least one degree of freedom.

10. The force transducer claim 1, wherein the members comprise grooves in which the optical fibres are disposed and secured to the members.

11. The force transducer of claim 10, wherein at least one member comprises holes arranged at groove ends and aligned with the grooves, and wherein the optical fibres accepted in the grooves continue in the holes.

12. A medical device configured for use in minimally invasive surgery, comprising the force transducer claim 1.

13. The medical device of claim 12, wherein the two structural members comprise coaxial through holes, wherein the plurality of optical fibres of the force transducer are arranged around a periphery of the coaxial through holes; the medical device further comprising a surgical tool and a conduit, wherein a proximal end of the surgical tool is mounted to a respective through hole of either one of the two members of the force transducer, and a distal end of the conduit is mounted to the respective through hole the other one of the two members, and wherein an elastic connecting piece couples the proximal end of the surgical tool to the distal end of the conduit, wherein the elastic connecting piece is arranged between the two structural members.

14. The force transducer of claim 1, wherein the plurality of optical fibres are at least three optical fibres.

15. The force transducer of claim 1, wherein the plurality of optical fibres are at least four optical fibres.

16. The force transducer of claim 1, wherein the two structural members comprise outer surfaces and respective coaxial through holes, and wherein the plurality of optical fibres are attached to the two structural members at locations between the outer surfaces and a perimeter of the coaxial through holes.

17. The force transducer of claim 1, wherein the stiffness is at least 95% determined by the plurality of optical fibres.

* * * * *